United States Patent [19]
Martin, Jr.

[11] Patent Number: 5,514,869
[45] Date of Patent: May 7, 1996

[54] METHOD FOR ESTIMATING THE PROBABILITIES OF DIGESTIVE TRACT DOSES DUE TO THE PASSAGE OF A SOLID RADIOACTIVE PARTICLE

[76] Inventor: James A. Martin, Jr., 22 Harvard Ct., Rockville, Md. 20850

[21] Appl. No.: 199,525

[22] Filed: Feb. 22, 1994

[51] Int. Cl.$^6$ .............................. G01T 1/161; G21H 5/02
[52] U.S. Cl. .............................................................. 250/303
[58] Field of Search ............................................. 250/303

[56] References Cited

U.S. PATENT DOCUMENTS

| | | | |
|---|---|---|---|
| 3,159,545 | 12/1964 | Kidwell et al. | 167/83 |
| 4,115,540 | 9/1978 | Digenis et al. | 424/1 |
| 4,591,720 | 5/1986 | Fuji et al. | 250/362 |

*Primary Examiner*—Bruce C. Anderson

[57] ABSTRACT

A new, improved method for estimating doses to body organs in the digestive system due to the passage of a solid radioactive particle through the digestive system. Normally, in this instance, doses to internal body organs are estimated (calculated) using mathematical models, because such doses cannot be measured routinely, if at all. Such models are used internationally as a basis for radiation protection standards. This new method applies to low penetrating emissions of a radionuclide, typically beta and/or alpha particles, low energy (soft) x-rays and/or gamma rays, and Auger electrons. The new method is physically correct in principle, in that it explicitly incorporates the location and velocity of a solid particle in the gastro-intestinal tract, whereas current and previously applied methods are incorrect, in this application. Moreover, this new method will provide estimates of the probability of dose, which is not considered in current methods of estimating such doses.

2 Claims, No Drawings

METHOD FOR ESTIMATING THE PROBABILITIES OF DIGESTIVE TRACT DOSES DUE TO THE PASSAGE OF A SOLID RADIOACTIVE PARTICLE

BACKGROUND OF THE INVENTION

1. Field of the Invention

This invention relates to the art and science of ionizing radiation dosimetry. In particular, to the estimation of doses to internal body organs in the digestive tract due to the passage of a solid particle carrying radionuclides which decay by emitting low penetrating ionizing radiations [i.e., beta and/or alpha particles, low energy (soft) x-rays and/or gamma rays, and/or Auger electrons]. In many cases these ionizing radiations are absorbed within the dimensions of a body organ. Such solid particles are generally called "radioactive particles". Such particles are typically of the dimensions of micrometers; they normally enter the body by inhalation and/or ingestion. Such particles can be insoluble or only slightly soluble in body fluids. These solid particles can be radioactive in themselves, or may carry radioactive matter with them. The radioactive matter may be soluble or partially soluble in body fluids.

Current dosimetry models adequately treat doses due to the dissolved portion of the radioactive material. This invention pertains to methods for estimating doses in the digestive system due to the passage of the undissolved portion of radioactive material in a solid particle. An incident has occurred in the nuclear industry in which a worker has ingested or inhaled a solid radioactive particle of the type described herein, so this matter is of practical and regulatory import.

2. Description of the Prior Art and Its Limitations

The current internal dose calculational methods (models) of the International Commission on Radiological Protection (ICRP), as employed in its publication ICRP No. 30, for example, calculate the ingestion dose to the mucus layer in the digestive tract, employing a dosimetry model, in which it is assumed that numerous solid radioactive particles are uniformly mixed in the inert matter in the digestive system, or portions thereof. The effective decay energy of a radioisotope is calculated using the effective half-life of the radioisotope in the organ of concern. The effective half-life incorporates the physical half-life of the radioisotope and a biological half-life of the (assumed, many) insoluble, or partly soluble, radioactive particles in the organ.

The ICRP modeling method does not apply to the case of the passage of a single solid particle, or a small group of particles— a particle is either in an organ, or it is not. In such a model, or method, the speeds and positions of an insoluble particle travelling through the digestive tract are not considered explicitly. Moreover, the ICRP method models the dose to the inert mucus layer of the digestive tract, rather than to living tissue.

The current ICRP No. 30 method has been used to set Federal Regulations and Standards governing the safety of workers and the public, e.g., 10 CFR Part 20. But it does not apply to the case of the passage of a single, solid radioactive particle through the digestive system.

Also, the ICRP No. 30 model does not incorporate the probability of dose. The probability of dose depends on the dimensions and composition of the solid radioactive particle, the energies of the radioactive emissions, and the time dependent probabilities of the location and velocity of a solid particle in the digestive system.

SUMMARY OF THE INVENTION

The new method incorporates both a physical model of the geometry of the exposure mode and the probability of the geometry, as a solid radioactive particle passes through the digestive system. The new method (model) is physically correct in that it correctly accounts for the physical phenomena that actually occur. Also, with this new method, probabilities of doses to living tissue actually affected by low penetrating ionizing radiations is calculated.

Physics of the New Method

As a solid radioactive particle approaches and then recedes from points in the digestive system, the ionizing radiations emitted may induce dose rates in living body tissues. The total dose delivered to a body point is the integral of the dose rates induced during the time of passage of the solid radioactive particle. The time of passage depends on the speed of the solid radioactive particle and the ranges of the ionizing radiations emitted.

As a solid particle moves through the digestive system, the dose rates in matter will vary throughout the range of the ionizing radiations, normally monotonically decreasing as distance from the solid radioactive particle and the amount of intervening matter increases. Such intervening matter can be the particle itself (self absorption), digested matter, mucus lining the digestive system, or living tissue.

As a simplified example of the new method, consider the simple case of an insoluble, solid particle travelling horizontally along the x axis at a constant speed v in a cylindrical digestive tract above a mucus layer 10 micrometers thick. Below the mucus is living tissue. Assume the insoluble particle carries with it one microcurie ($3.7 \times 10^4$ Becquerel, Bq) of the radioisotope cobalt-60 (Co-60). Consider the question: what is the total dose at a point in living tissue just below the mucus layer, as delivered by the beta particles emitted by the decaying Co-60, as the insoluble, solid particle moves at a constant speed v, first approaching the tissue point and then receding from it? For this simple case, ignore self-absorption by the insoluble particle (but this can be accommodated in a complete modeling—e.g., see "Hot Particle Self-Absorption Factor", N. Tsoulfandis, H. P. Jr., pp. 841–842, June 1991). Also ignore solubility and radioactive decay.

For a stationary beta emitting radionuclide, data from Cross, et al (Cross, W. G., Freedman, N. O. and Wong, P. Y., "Beta Dose Distributions from Point Sources in an Infinite Water Medium", H. P. Jr., pp. 160–171, August 1992) show that, within a factor of two, the beta dose rate in water from a Co-60 beta particles follows an inverse distance squared relationship to a range of 50 micrometers, or so, the dose rate at 10 micrometers range being about 200 centiGray/sec (cGy/sec, or rads/second) per microcurie. Since tissue is mostly water, assume this value and this relationship. [In the Cross, et al, nomenclature, $R^2$, J'(R)=constant implies an inverse distance squared relationship.]

For the moving solid particle, the total dose J at the point is given by the integral of the dose rate J'(t) at the point as a function of time t:

$$J = \int_0^\infty J'(t)dt$$

For a constant solid particle speed, the total dose induced at the point is given by the integral of the dose rates induced as a function of the position of the solid particle:

$$J(x) = \int_{-\infty}^{\infty} J'(x)dx/v$$

where

J'(x)= dose rate at the point when the particle is at horizontal distance x, and dt=dx / v.

Now, in this geometry, when the particle is at a horizontal stant range x, it is at a distance R from the point, where R is the hypotenuse of a right triangle of sides R, 10, and x, and $R^2=x^2+10^2$.

In this case,

J'(x)=J'(10) (10/R)$^2$, where

J'(10)=dose rate at the tissue point when the particle is just above this point (position of closest approach), with the 10 micrometer mucus layer intervening.

Since J'(10) is a constant in this example:

$$J(10)v = J'(10)10^2 \int_{-\infty}^{\infty} dx/(x^2 + 10^2)$$

J(10)=10πJ'(10)/v

Then:
where J(10) is the integrated (total) dose at the tissue point in cGy (rads), and v is the speed of the particle (constant, here) as it passes above the point being considered, in micrometers/sec. (Any consistent set of units may be used; the conversion relationships 3.7×10$^4$ Becquerels:=1 microcurie, and 1 rad =1 cGy may be used to convert units.) Under these assumptions, the dose at any distance other than zero may be obtained by substituting the distance (in micrometers) for 10 in the above equation.

A value for v may be obtained from estimates of the length of the intestines [e.g., 5 ft (1.524 meters)], and of the time spent by the insoluble particle in the body (e.g., 24 hours, or 86400 seconds), to give an estimated speed in this example of 17.6 micrometers per second.

Substituting in the above equation, the result is a total beta dose estimate of 357 cGy per microcurie, at the tissue point. (As stated in Report No. 106 of the National Council on Radiation Protection and Measurements, up to 10 microcurie Co-60 particles have been found in the nuclear industry.) Doses would be increased in the vicinity of a slower moving solid, insoluble particle, but decreased when the beta emissions are attenuated by more matter or self absorption in the solid particle.

Incorporation of Probability of Dose

This new method (model) takes into account the stochastic nature of the travel of a solid radioactive particle through the digestive tract. Current dosimetry models, including the ICRP 30 model, ignore this aspect of the phenomena.

As a solid radioactive particle travels through the digestive system, its low penetrating ionizing radiation emissions may be partially absorbed by inert matter in the digestive tract. For example, the radioactive particle may be located in the middle of inert material on the bowel. The inert material in the bowel can shield living tissue by absorbing part or all of the energy of low penetrating radiations. In this event the dose to the living tissue can be much lower than if the solid particle happens to be located at or near the edge of the inert material, i.e., close to living tissue. The potential for shielding by inert matter is also not accounted in current or previous dosimetry models for a solid radioactive particle in the digestive tract.

A solid radioactive particle may proceed through the digestive system in starts and stops. While stopped, the particle will induce the highest dose rates in matter in its immediate vicinity - matter that can be living tissue. This, also, is not modeled currently in other approaches, including the ICRP 30 modeling.

Data regarding the speeds of travel of a solid particle in the digestive tract can be obtained from data obtained from human exposures (e.g., see U.S. NRC Event Report No. 16091). The probability of the location of a solid particle in a cross-section of the digestive system may have to be obtained from carefully controlled and monitored experiments yet to be performed. Considering the stochastic nature of the phenomena, the latter probability may be estimated to first order by assuming that the probability is proportional to available cross-sectional area, for which the probability p(r) dr is 2r dr/R$^2$, where r is the distance from the center of the inert matter, and R is the radius of the inert matter, where the cross-section is assumed to be a circle.

The accommodation of the stochastic nature of the travel of a solid particle through the digestive system is a major improvement over current and previous dose modeling for the subject case.

PREFERRED EMBODIMENT

Incorporation of this invention (method), or results of its applications, in Federal and State Regulations and/or Standards regarding radiation protection standards for workers and the public, and its use in the nuclear industry for assessing conformance with such regulations, including industry national standards, is the preferred embodiment. The proximate embodiment would be a computer code for performing the necessary and desirable calculations.

I claim:

1. A method for calculating the probabilities of doses to body matter induced by low penetrating ionizing radiation emanating from radionuclides as said radionuclides are transported through the digestive system in a solid particle that is insoluble or partially soluble in body fluids, comprising the steps of:

(a) estimating the dimensions and composition of the digestive system;

(b) estimating the probabilities of the location and velocity of the solid particle within the digestive system at any point and time during the passage of said particle through the body;

(c) calculating the absorption and attenuation effects of matter in the body on low penetrating ionizing radiation emitted by the radionuclides in said particle;

(d) calculating the dose rates induced at various points in the body at various times using the results from steps (a) through (c) above;

(e) integrating said dose rates to calculate total doses accumulated at various points in the body due to the passage of the radionuclides in said particle; and (f) calculating the probabilities of doses to body matter using the results from steps (a) through (e) above.

2. A method for calculating doses to body matter induced by low penetrating ionizing radiations emanating from radionuclides as said radionuclides are transported through the digestive system in a solid particle that is insoluble or partially soluble in body fluids, comprising the steps of:

(a) estimating the dimensions and composition of the digestive system;

(b) estimating the speeds and paths of the solid particle as said particle passes through the digestive system;

(c) calculating the absorption and attenuation effects of matter in the body on low penetrating ionizing radiations emitted by the radionuclides in said particle;

(d) calculating the dose rates induced at various points in the body at various times using the results from steps (a) through (c) above; and (e) integrating said dose rates to calculate total doses accumulated at various points in the body due to the passage of the radionuclides in said particle.

* * * * *